(12) United States Patent
Mather et al.

(10) Patent No.: US 10,252,009 B2
(45) Date of Patent: Apr. 9, 2019

(54) HEAT-CURLING POLYMERIC NEEDLE FOR SAFE DISPOSAL

(71) Applicants: SYRACUSE UNIVERSITY, Syracuse, NY (US); Patrick T. Mather, Syracuse, NY (US); Pine Yang, Syracuse, NY (US)

(72) Inventors: Patrick T. Mather, Syracuse, NY (US); Pine Yang, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 275 days.

(21) Appl. No.: 14/783,423

(22) PCT Filed: Apr. 8, 2014

(86) PCT No.: PCT/US2014/033338
§ 371 (c)(1),
(2) Date: Oct. 8, 2015

(87) PCT Pub. No.: WO2014/168951
PCT Pub. Date: Oct. 16, 2014

(65) Prior Publication Data
US 2016/0074597 A1 Mar. 17, 2016

Related U.S. Application Data

(60) Provisional application No. 61/809,502, filed on Apr. 8, 2013.

(51) Int. Cl.
*A61M 5/32* (2006.01)
*B29C 47/00* (2006.01)
(Continued)

(52) U.S. Cl.
CPC ......... *A61M 5/329* (2013.01); *B29C 47/0016* (2013.01); *B29C 47/0023* (2013.01);
(Continued)

(58) Field of Classification Search
CPC .......... A61M 5/329; A61M 2005/3212; A61M 2005/3284
See application file for complete search history.

(56) References Cited

U.S. PATENT DOCUMENTS 4,728,320 A * 3/1988 Chen ................... A61M 5/3213
604/110
8,250,729 B2 * 8/2012 Lee ..................... A61B 17/205
29/527.2

(Continued)

OTHER PUBLICATIONS

Definition of needle (cited on Oct. 16, 2017).*
Polyether ether ketone glass transition temperature (Wikipedia Jul. 9, 2018).*

*Primary Examiner* — Andrew Gilbert
*Assistant Examiner* — Dung Ulsh
(74) *Attorney, Agent, or Firm* — Bond Schoeneck and King PLLC; David Nocilly; George McGuire

(57) ABSTRACT

A needle having shaft that forms a tip and a portion proximate to the tip that is formed from a shape memory polymer. The shaft of the needle may be programmed to curl from a straight configuration to a curved configuration upon triggering by heat, thereby moving the sharp tip and providing a non-stick needle for safe and easy disposal.

9 Claims, 9 Drawing Sheets

(51) Int. Cl.
  *B29C 47/92* (2006.01)
  *B29D 23/00* (2006.01)
  B29L 31/00 (2006.01)
  B29K 33/00 (2006.01)

(52) U.S. Cl.
  CPC .......... *B29C 47/0066* (2013.01); *B29C 47/92* (2013.01); *B29D 23/001* (2013.01); *A61M 2005/3212* (2013.01); *A61M 2005/3284* (2013.01); *A61M 2205/0266* (2013.01); *A61M 2207/00* (2013.01); *B29C 2947/92704* (2013.01); *B29K 2033/12* (2013.01); *B29K 2995/0012* (2013.01); *B29L 2031/7544* (2013.01)

(56) References Cited

U.S. PATENT DOCUMENTS

| | | | |
|---|---|---|---|
| 2006/0202385 A1* | 9/2006 | Xu | A61M 37/0015 264/219 |
| 2009/0177161 A1* | 7/2009 | McGuckin, Jr. | A61B 17/3417 604/164.11 |
| 2009/0209923 A1* | 8/2009 | Linderoth | A61M 5/32 604/272 |
| 2010/0193980 A1* | 8/2010 | Ghosh | B23D 79/00 264/28 |

\* cited by examiner

HEAT-CURLING POLYMERIC NEEDLE FOR SAFE DISPOSAL

CROSS-REFERENCE TO RELATED APPLICATIONS

The present application claims priority to U.S. Provisional Application No. 61/809,502, filed on Apr. 8, 2013.

BACKGROUND OF THE INVENTION

1. Field of the Invention

The present invention relates to hypodermic needles and, more particularly, to a needle having a curlable tip formed from a shape memory polymer.

2. Description of Related Art

Improper and unsafe needle-syringe disposal is a worldwide healthcare issue. It has been well documented especially in developing countries which cause tens of millions of hepatitis and HIV infections each year. The conventional steel needle requires high temperature for incineration and will generate a large amount of waste. Even after disabling the needles, they are still sharp hazards and potentially dangerous for the recycling workers. Auto-disable needle-syringes have been developed in recent years to solve the problem of reusing, most of these devices worked by preventing the syringes plunger from being withdrawn after injection. These needles are complicated designs that involve multiple actuating parts, including sleeves and/or springs. Thus, the needle disposal and recycling problem has not yet been solved.

BRIEF SUMMARY OF THE INVENTION

The present invention comprises a needle having a tip formed from a shape memory polymer (SMP). SMPs are a class of stimuli-responsive materials that can undergo a shape change based on specific stimuli or conditions. SMPs have been widely used in biomedical devices such as deployable stents and aneurysm occlusion devices. A conventional steel needle is replaced with a polymer needle having a programmable SMP, thus providing a disabling process that is easy, fast and safe. In a preferred embodiment, the needle tip will curl and become non-stick upon triggering by heat, thereby transitioning to a curled and non-stick shape for safe and easy disposal. There present invention may be manufactured from a commercially available polymer that features good shape memory characteristics, such as high molecular weight poly(methyl methacrylate) (PMMA).

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1A:
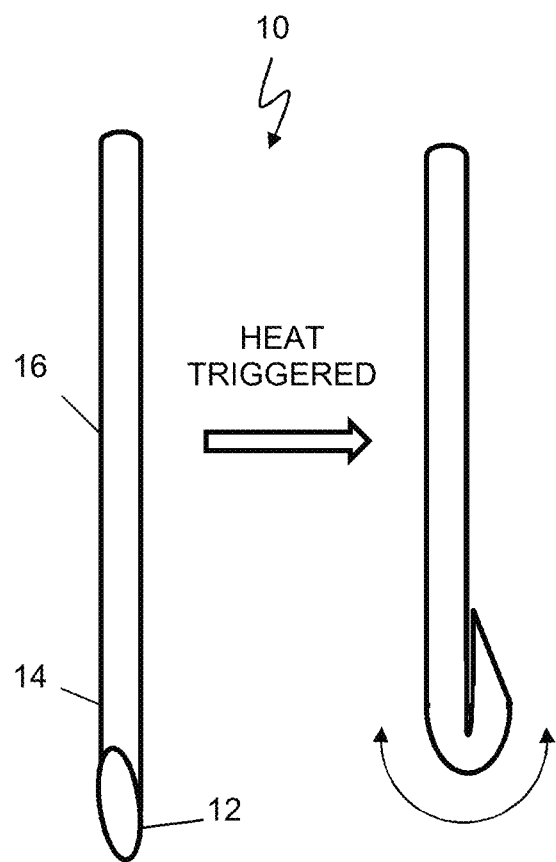
FIG. 1A is a schematic of a shape memory needle that transitions to a non-stock configuration when triggered by heat according to the present invention.
Figure 1B:
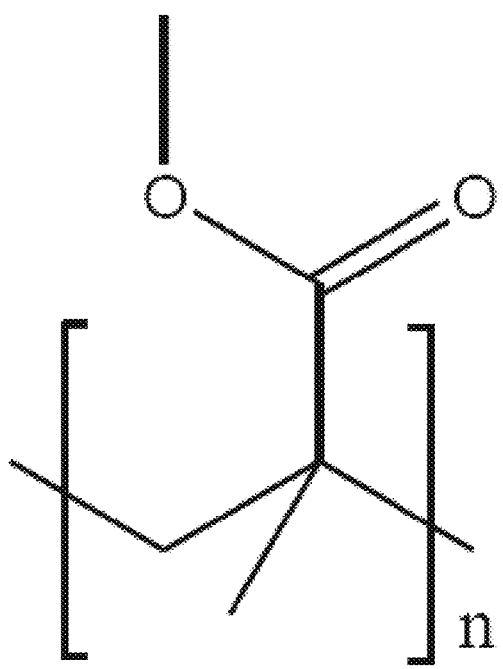
FIG. 1B is a schematic of the polymer structure of an exemplary embodiment of a needle according to the present invention.

Referring now to the drawings, wherein like reference numerals refer to like parts throughout, there is seen in FIG. 1A a schematic of a safe needle system 10 according to the present invention, where heat triggering results in curling of a needle tip 12 when a portion 14 of needle shaft 16 curves, such as by about 180 degrees. As seen in FIG. 1A, a preferred embodiment of system 10 comprises the use of high molecular weight poly(methyl methacrylate) (PMMA).

Figure 2A:
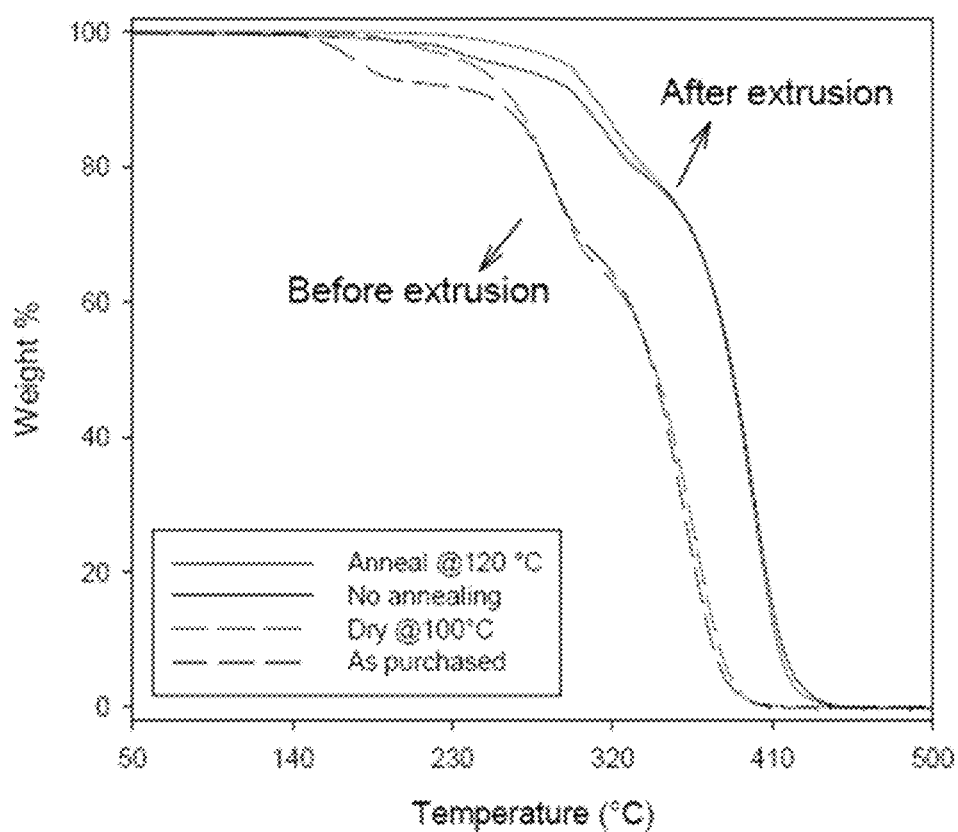
FIG. 2A is a graph showing various characteristics of a preferred embodiment before and after extrusion and with and without an annealing process.
Figure 2B:
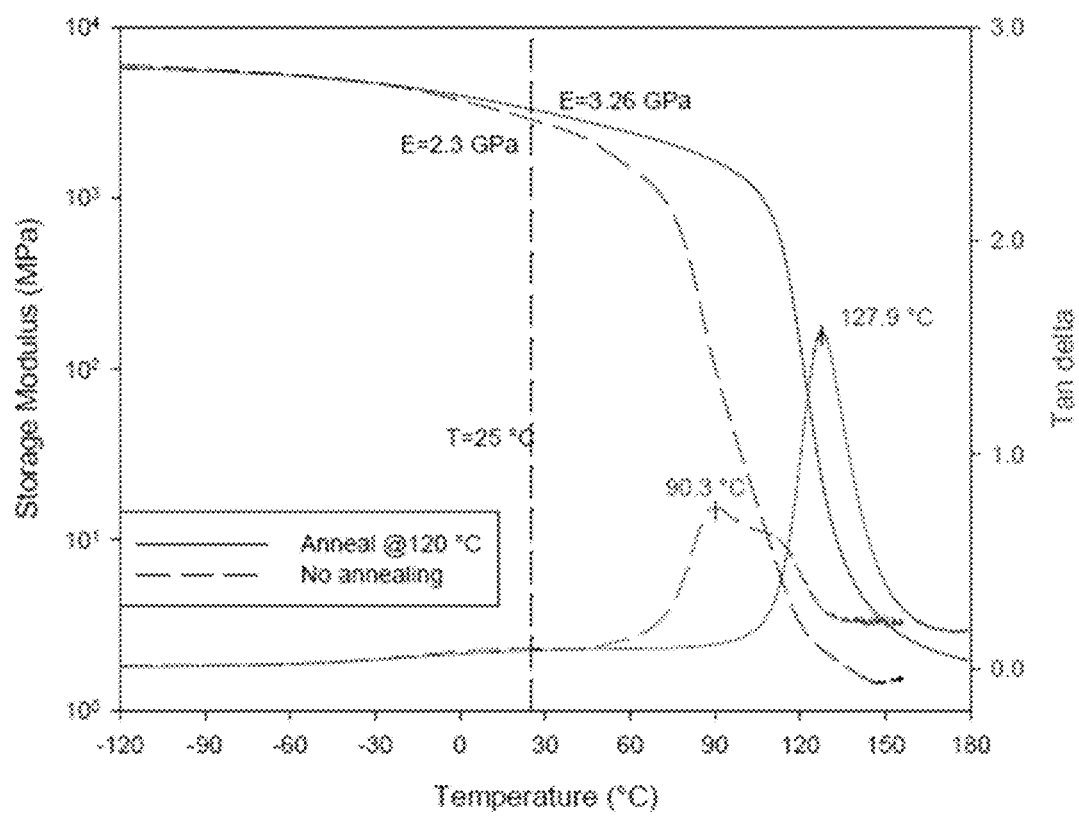
FIG. 2B is a graph showing various characteristics of a preferred embodiment before and after extrusion and with and without an annealing process.

As seen in FIGS. 2A and 2B, TGA analysis on PMMA before and after extrusion and thermomechanical properties on extruded PMMA rod with and without annealing process demonstrate that the present invention can provide the requisite parameters for a hypodermic needle.

Figure 3A:
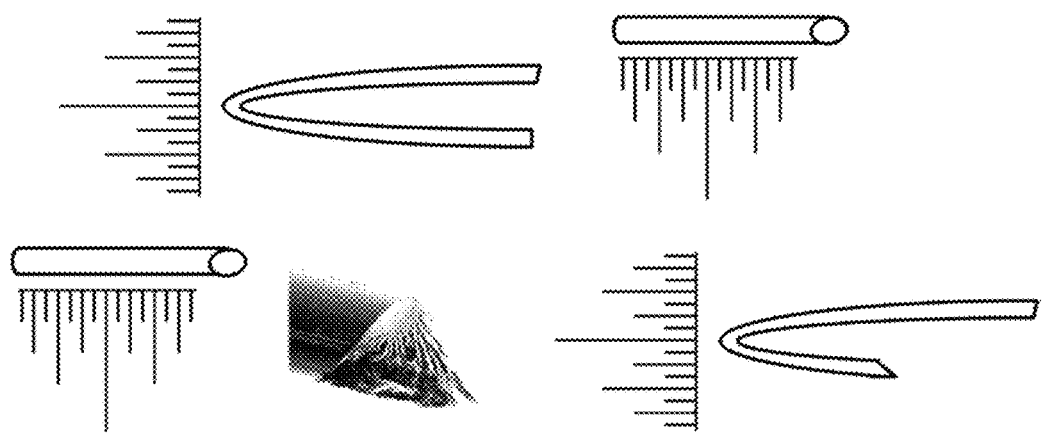
FIG. 3A is a series of photographs of a PMMA extruded strand is set in (i) a permanent bent state, (ii) and (iii) temporarily straightened for use as a needle, and then (v) recovered with heating.
Figure 3B:
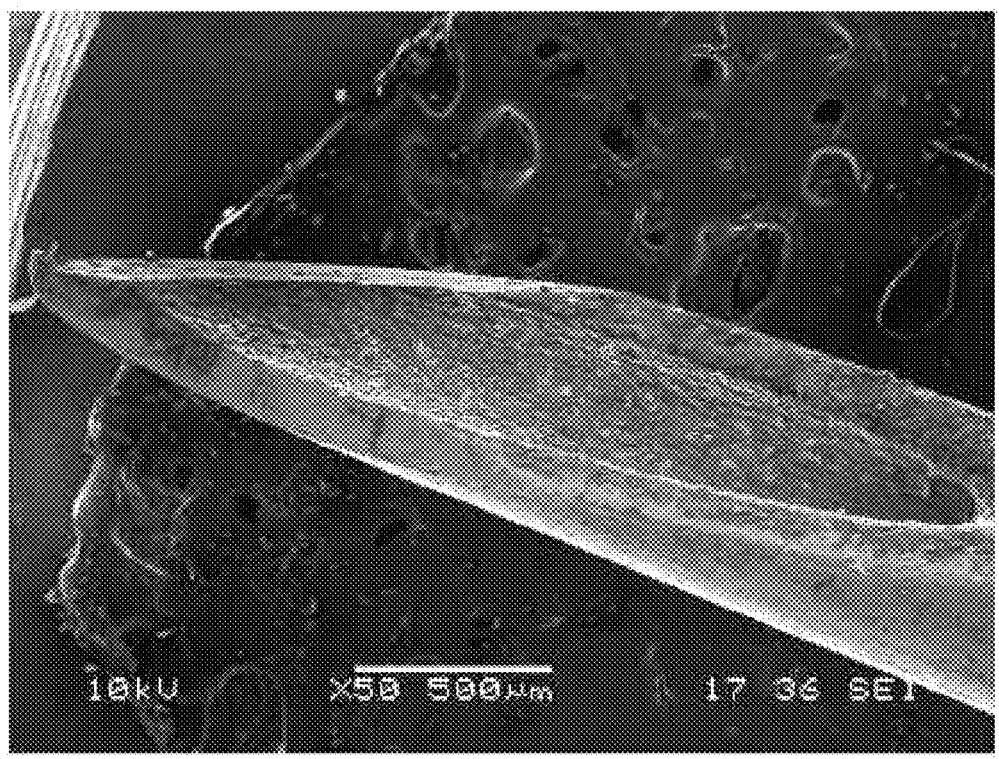
FIG. 3B is a micrograph of a sharp PMMA needle similar to a BD 22 gauge needle tip formed using a cryogenic torque fracture process.

As seen in FIG. 3A, testing of the present invention as described herein involved the use of a PMMA extruded strand that was set in (i) a permanent bent state, (ii) and (iii) temporarily straightened for use as a needle, and then (v) recovered with heating. Referring to FIG. 3B, cryogenic torque fracture yielded sharp PMMA needles that can form a BD 22 gauge needle tip.

Figure 4:
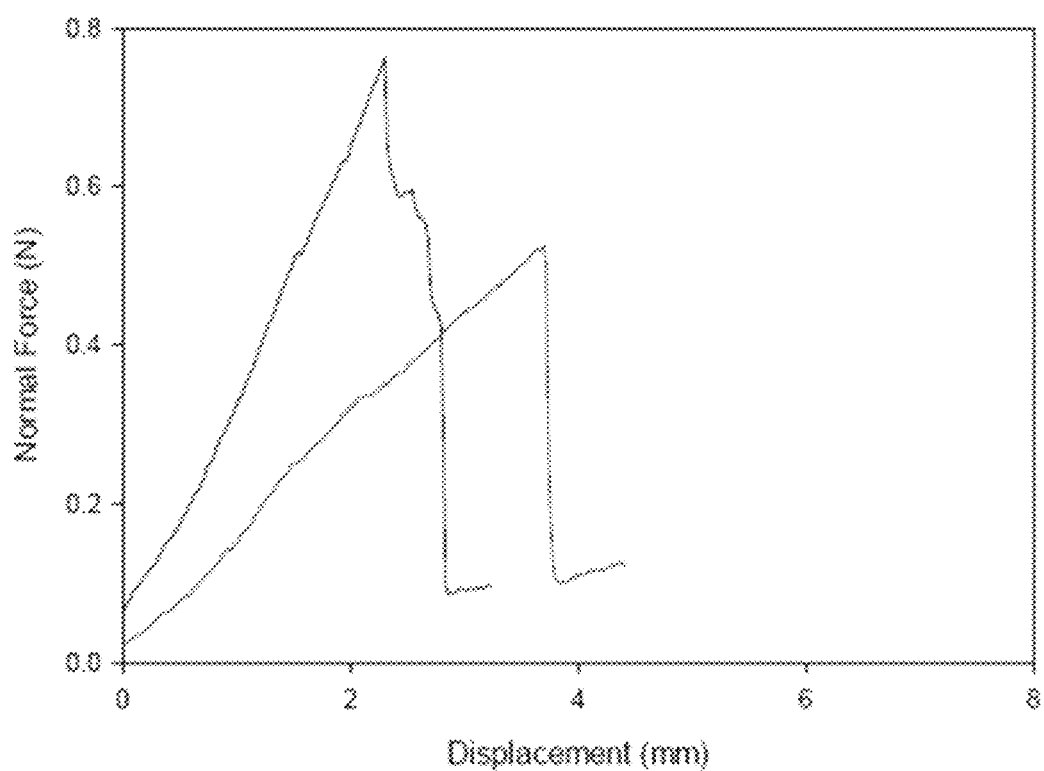
FIG. 4 is a force-penetration curve for PMMA freeze-fracture tip on a skin model according to the present invention where a polymer needle diameter of 750 μm and loading speed of 20 μm/s was used.

A skin model composed of ballistic gel and a layer of nitrile rubber may be used to evaluate a needle according to the present invention and was used to generate a force-penetration curve for a PMMA freeze-fracture tip. A polymer needle diameter of 750 μm and a loading speed of 20 μm/s was used to determine efficacy of the present invention on skin using the skin module, with the results seen in FIG. 4.

Figure 5:
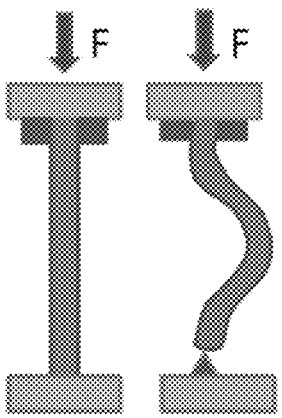
FIG. 5 is a schematic of critical buckling force.
Figure 6:
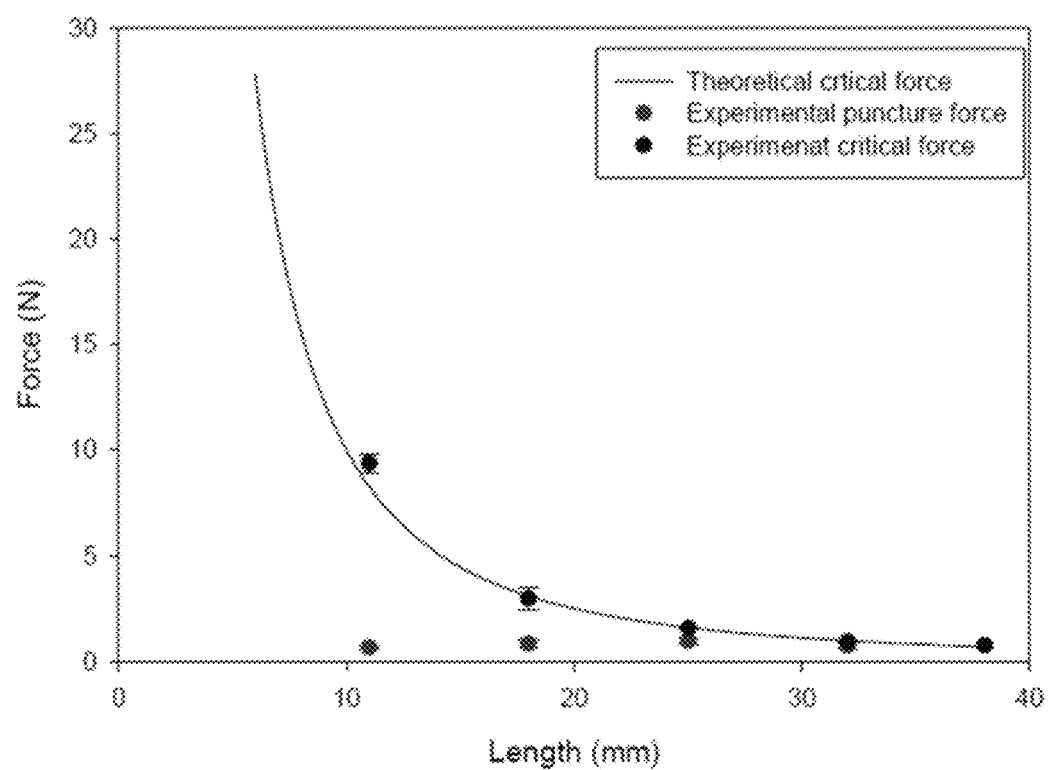
FIG. 6 is a graph of puncture force dependence on polymer needle length.

As seen in FIG. 5, a buckling model was used to determine critical buckling force and puncture force dependence on polymer needle length. As seen in FIG. 6, with increasing length of polymer needle, the critical force for penetration increases. The present invention of a heat curling needle for safe disposal was demonstrated, and controlled thermal and mechanical properties were achieved by extrusion and additional annealing processing.

EXAMPLE

High molecular weight PMMA with 540 KDa was used to form a needle according to the present invention. The polymer was pre-dried at 100° C. prior to extrusion at 205° C. The thermal stability and glass transition (Tg) of PMMA fiber before and after extrusion were compared. An annealing process was performed after extrusion at 120° C. for following characterizations. Shape memory characterization was performed using dynamic mechanical analysis, and the ability of the hotpress PMMA film to fix a tensile strain and recover back to the original shape was measured. The heat-curling PMMA needle fabrication was demonstrated as follows: (1) Set the permanent curling shape at 130° C. for 24 h, (2) Program temporary straight shape at 110° C. for 2 min with weight on, (3) Fix and unload the straight rod at RT, (4) Create a sharp the tip, (5) Recover to the permanent curling shape at 150° C. A sharp tip creation was achieved by freeze fracture in liquid nitrogen. A skin model was developed for needle buckling analysis containing thick ballistic gel as a mimic of dermis and a layer of Nitrile Butadiene rubber (Nitrile glove) on the top as a mimic of epidermis. Puncture forces were measured with various needle lengths. The effect of needle length on critical buckling force was investigated and compared with theoretical prediction.

The extruded PMMA was pre-dryed at 100° C. before extrusion and annealed at 120° C. The PMMA after extrusion exhibited good thermal stability and a Tg of 111° C. It also showed a high elastic modulus of 3.4 GPa at RT. The hotpress PMMA film exhibited excellent shape fixing with a fixing ratio of 99% over three cycles. Due to the creep effect, recovery ratio was 68% on the first cycle and gradually increased to 95% on the third cycle.

With the aid of the skin model, the puncture forces of PMMA needles with a diameter of 0.75 mm were measured. It did not reveal a strong dependence on needle length with an average of 0.8 N higher than the 0.49 N of commercial BD 22 gauge needle. The critical buckling force with various PMMA needle lengths was also investigated. The length dependence was well predicted by Euler's buckling theory.

This example demonstrates the utility of shape memory curling needle for safe disposal and recycling purpose. High molecular weight PMMA fibers exhibited good shape fixing and recovery ratios. The needle tip sharpness was achieved by freeze fracture. With the help of the skin model that was developed, the puncture force was measured and it did not reveal a dependence on needle length. However, the needle critical buckling force was well predicted by Euler's theory and showed strong dependence on length. This example provides a simple way for fabricating a polymeric non-stick needle for easy and safe disposal. The present invention also encompasses further improvements that should be evident to those of skill in the art, such as replacing a solid PMMA fiber with hollow tube for needle fabrication.

What is claimed is:

1. A needle, comprising:
a hollow shaft including a tip and a portion proximate to said tip that is formed from a shape memory polymer having a glass transition temperature above 100 degrees Celsius; and
wherein said portion will transition from a temporary configuration that is straight to a permanent configuration that has a curve when said portion is heated to at least said glass transition temperature;
wherein said portion comprises a film formed from a plurality of hot pressed 540 KDa poly(methyl methacrylate) fibers having a glass transition temperature of 111 degrees Celsius; and
wherein said curve of said permanent configuration is sufficient to bend said hollow shaft about 180 degrees when said portion is heated to at least said glass transition temperature.

2. The needle of claim 1, wherein said portion has an elastic modulus of about 3.4 GPa at room temperature.

3. The needle of claim 2, wherein said tip comprises a freeze fractured portion of said hollow shaft.

4. A method of using a needle, comprising the steps of:
providing a needle having a hollow shaft including a tip and a region proximate to said tip that is formed from a shape memory polymer having a glass transition temperature above 100 degrees Celsius, wherein said portion will transition from a temporary configuration that is straight to a permanent configuration that has a curve when said portion is heated to at least said glass transition temperature, wherein said portion comprises a film formed from a plurality of hot pressed 540 KDa poly(methyl methacrylate) fibers having a glass transition temperature of 111 degrees Celsius, and wherein said curve of said permanent configuration is sufficient to bend said hollow shaft about 180 degrees when said portion is heated to at least said glass transition temperature;
using said needle to inject a subject;
heating said needle to above 100 degrees Celsius until said portion transitions from said temporary configuration to said permanent configuration.

5. The method of claim 4, wherein said portion has an elastic modulus of about 3.4 GPa at room temperature.

6. The method of claim 5, wherein said tip comprises a freeze fractured portion of said shaft.

7. A method of manufacturing a needle, comprising the steps of:
extruding a needle having a hollow shaft including at least a portion formed from a shape memory polymer having a glass transition temperature above 100 degrees Celsius that will change from a temporary configuration that is straight to a permanent configuration that has a curve when said portion is heated above a said glass transition temperature wherein said portion comprises a film formed from a plurality of hot pressed 540 KDa poly(methyl methacrylate) fibers having a glass transition temperature of 111 degrees Celsius, and wherein said curve of said permanent configuration is sufficient to bend said hollow shaft about 180 degrees when said portion is heated to at least said glass transition temperature;
setting said permanent configuration by heating said needle above a temporary temperature;
programming said temporary configuration by heating said needle under a load to a second temperature that is lower than said temporary temperature; and
freeze fracturing said shaft to form a sharp tip.

8. The method of claim 7, wherein the step of freeze fracturing said shaft to form a sharp tip comprises cooling said shaft with liquid nitrogen and applying torque.

9. The needle of claim 7, wherein said portion comprises poly(methyl methacrylate).

* * * * *